US009714201B2

(12) United States Patent
Theuerkauf et al.

(10) Patent No.: US 9,714,201 B2
(45) Date of Patent: Jul. 25, 2017

(54) ISONONYLAMINES FROM 2-ETHYLHEXANOL, PROCESSES FOR THEIR PREPARATION, AND THEIR USE

(71) Applicant: Oxea GmbH, Oberhausen (DE)

(72) Inventors: Jens Theuerkauf, Riedstadt (DE); Guido D. Frey, Riedstadt (DE); Matthias Eisenacher, Wesel (DE); Kristina Kockrick, Düsseldorf (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 89 days.

(21) Appl. No.: 14/413,444

(22) PCT Filed: Jun. 19, 2013

(86) PCT No.: PCT/EP2013/001812
§ 371 (c)(1),
(2) Date: Jan. 8, 2015

(87) PCT Pub. No.: WO2014/008979
PCT Pub. Date: Jan. 16, 2014

(65) Prior Publication Data
US 2015/0152023 A1 Jun. 4, 2015

(30) Foreign Application Priority Data

Jul. 13, 2012 (DE) .................. 10 2012 014 395

(51) Int. Cl.
| | | |
|---|---|---|
| C07C 1/24 | (2006.01) | |
| C07C 209/26 | (2006.01) | |
| C07C 211/03 | (2006.01) | |
| C07C 333/16 | (2006.01) | |
| C07C 45/50 | (2006.01) | |
| C10M 135/18 | (2006.01) | |

(52) U.S. Cl.
CPC ............... *C07C 1/24* (2013.01); *C07C 45/50* (2013.01); *C07C 209/26* (2013.01); *C07C 211/03* (2013.01); *C07C 333/16* (2013.01); *C10M 135/18* (2013.01); *C07C 2521/04* (2013.01)

(58) Field of Classification Search
None
See application file for complete search history.

(56) References Cited

U.S. PATENT DOCUMENTS

| 2,468,764 A | 5/1949 | Laurent |
| 2,919,973 A * | 1/1960 | Stillwell ............. B01J 21/04 |
| | | 423/626 |
| 3,483,253 A | 12/1969 | Adam et al. |
| 3,527,809 A | 9/1970 | Pruett et al. |
| 4,148,830 A | 4/1979 | Pruett et al. |
| 4,247,486 A | 1/1981 | Brewester et al. |
| 4,283,562 A | 8/1981 | Billig et al. |
| 4,563,294 A * | 1/1986 | Geymayer .......... C10M 173/02 |
| | | 508/404 |
| 4,684,750 A * | 8/1987 | Kessen ............. C07C 29/175 |
| | | 568/882 |
| 5,530,127 A * | 6/1996 | Reif ................ C07C 209/16 |
| | | 544/106 |
| 2011/0230342 A1 | 9/2011 | Klingelhoefer et al. |

FOREIGN PATENT DOCUMENTS

| DE | 1257782 B | 1/1968 |
| DE | 1518118 A1 | 11/1969 |
| DE | 2048750 A1 | 4/1972 |
| DE | 2737633 B1 | 2/1979 |
| GB | 313426 A | 6/1929 |
| WO | 2003029180 A1 | 4/2003 |
| WO | 2009146988 A2 | 12/2009 |
| WO | WO2011113786 | * 9/2011 |

OTHER PUBLICATIONS

English translation of WO2011113786, pp. 30, Sep. 22, 2011.*
Ma et al., "Hydrofromylation of mixed octenes catalyzed by supported rhodium-based catalyst," Fuel Processing Technology 90(2009) 1241-1246.*
Robichaud et al., "First example of direct reductive amination of aldehydes with primary and secondary amines catalyzed by water soluble transition metal catalysts," Tetrandedron Letters 47(2006) 3633-3636.*
International Search Report dated Sep. 26, 2013.
Scharfe, G., "Convert butenes to high octane oligomers", Hydrocarbon Processing, Apr. 1973, pp. 171-173.
International Preliminary Report on Patentability dated Jan. 22, 2015.

* cited by examiner

*Primary Examiner* — Paul A Zucker
*Assistant Examiner* — Mark Luderer
(74) *Attorney, Agent, or Firm* — Michael W. Ferrell

(57) ABSTRACT

Process for preparing isononylamines starting out from 2-ethylhexanol, characterized in that (a) 2-ethylhexanol is dehydrated in the presence of a catalyst to form octene; (b) the octene obtained in step a) is reacted with carbon monoxide and hydrogen in the presence of a transition metal compound of group VIII of the Periodic Table of the Elements to form isononanal; and (c) the isononanal obtained in step b) is converted into isononylamines.

21 Claims, No Drawings

ISONONYLAMINES FROM 2-ETHYLHEXANOL, PROCESSES FOR THEIR PREPARATION, AND THEIR USE

CLAIM FOR PRIORITY

This application is a national phase application of PCT/EP2013/001812 FILED Jun. 19, 2013 which was based on application DE 10 2012 014 395.8 FILED Jul. 13, 2012. The priorities of PCT/EP2013/001812 and DE 10 2012 014 395.8 are hereby claimed and their disclosures incorporated herein by reference.

TECHNICAL FIELD

The present invention relates to isononylamines starting out from 2-ethylhexanol, a process for preparing them by dehydration of 2-ethylhexanol, hydroformylation of the resulting octene mixture to form isononanal and conversion into the corresponding isononylamines and also their use.

BACKGROUND

Aliphatic amines are important organic intermediates which are prepared on a large industrial scale. For example, they are processed further to produce pharmaceutical products, agrochemicals or dyes or they serve as additive in surface-active formulations, as corrosion inhibitor and as additives in lubricants, for example in the form of their dithiocarbamates or corresponding salts, for improving the abrasion resistance of mechanical apparatuses which are operated under high pressure or as auxiliaries for the paper, textile and rubber industries. The short-chain amines having fewer than six carbon atoms per alkyl group and the fatty amines having from about 8 to 24 carbon atoms per alkyl chain are of particular industrial importance. While fatty amines were firstly produced from natural fatty acids, fatty amines have for some years also been obtained on the basis of petrochemical raw materials by processes which have become established many years ago for the preparation of short-chain amines.

Thus, the reductive amination of aldehydes and ketones by means of ammonia, primary or secondary amines leads to primary, secondary or tertiary amines. Amine formation can, for example, be described by the following reaction stages:

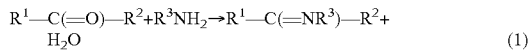
(1)

(2)

In the first reaction stage, an imine intermediate ($R_3$=hydrogen) is formed by reaction of an aldehyde ($R^1$=alkyl and $R^2$=hydrogen) or a ketone ($R^1$ and $R^2$=alkyl) with ammonia or an azomethine intermediate or Schiff base ($R^3$=alkyl) is formed by reaction with a primary amine. These intermediates are subsequently catalytically hydrogenated, either directly in one step or after isolation in the absence of water in separate reaction stages. The catalytic hydrogenation can be carried out in the presence of conventional hydrogenation catalysts such as nickel or cobalt catalysts which are activated by additions of chromium (DE 1257 782 A1, DE 2048 750 A1).

If secondary amines are reacted with aldehydes or ketones, a hydrogen atom has to be bound to the carbon atom adjacent to the carbonyl group so as to enable this hydrogen atom to be eliminated in the form of water to form an enamine. The subsequent catalytic hydrogenation then leads to tertiary amines.

If ammonia is reacted with aldehydes or ketones, primary amines are firstly formed and these then react with further aldehyde or ketone via the azomethine intermediate to form the secondary amine which can then react further in an analogous way to form tertiary amines. The product distribution can be controlled by the amount of ammonia used. Large molar excesses of ammonia promote the formation of primary amines.

Apart from the reductive amination of carbonyl compounds, the amination of alcohols or ammonolysis in the presence of hydrogen catalysts is also carried out industrially:

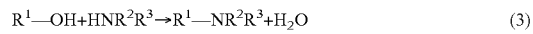
(3)

If ammonia ($R^2$ and $R^3$=hydrogen) is reacted, a primary amine is firstly formed and this reacts further with further alcohol to form a secondary amine which can react analogously to form a tertiary amine. In this reaction, too, the product distribution can be controlled by means of the amount of ammonia used. A large molar excess of ammonia promotes the formation of the primary amine.

Suitable hydrogenation catalysts are nickel, cobalt, iron or copper catalysts, e.g. Raney nickel (U.S. Pat. No. 2,782,237, U.S. Pat. No. 2,182,807). The amination of alcohols can also be carried out in the presence of hydrogen.

Further processes for preparing amines encompass the reaction of alkyl halides with ammonia, the addition of ammonia onto olefinic double bonds, the catalytic hydrogenation of carboxylic nitriles and the catalytic reduction of nitroalkanes by hydrogen (Ullmanns Encyklopädie der technischen Chemie, 4th edition, volume 7, 1974, pages 374-389; volume 11, 1976, pages 447-452).

Isononylamine (CAS number 27775-00-4) and diisononylamine (CAS number 28454-70-8) are of industrial importance as supplement and also as additives in lubricants, for example in the form of their dithiocarbamates or corresponding salts, for improving the abrasion resistance of mechanical apparatuses which are operated under high pressure, as additive in corrosion inhibitors or for hydraulic fluids. Isononylamine contains predominantly 3,5,5-trimethylhexylamine and diisononylamine contains predominantly di(3,5,5-trimethylhexyl)amine as main isomer.

The C-9 hydrocarbon skeleton 3,5,5-trimethylhexyl is based on the petrochemical intermediate isobutene which is dimerized to diisobutene in the presence of acid catalysts and separated off by distillation from the higher oligomers which are likewise formed (Hydrocarbon Processing, April 1973, pages 171-173; Ullmann's Encyclopedia of Industrial Chemistry, 6th. Ed., 2003, Vol. 6, page 3). Diisobutene consists essentially of the isomeric octenes 2,4,4-trimethyl-1-pentene and 2,4,4-trimethyl-2-pentene and can be converted by means of the oxo reaction or hydroformylation reaction with carbon monoxide and hydrogen in the presence of rhodium or cobalt catalysts into the corresponding aldehyde 3,5,5-trimethylhexanal (Ullmann's Encyclopedia of Industrial Chemistry, 6th. Ed., 2003, Vol. 2, pages 68, 75; DE 2737633 A). The hydrogenation gives the alcohol 3,5,5-trimethylhexanol which is used, for example, as high-boiling solvent (Ullmann's Encyclopedia of Industrial Chemistry, 6th. Ed., 2003, Vol. 2, pages 22, 33).

The most important raw materials source for isobutene is the C4 fraction from the steam cracking of naphtha. Its availability compared to the C2 and C3 cracking products can be controlled via the conditions of steam cracking and is guided by market circumstances.

Firstly, 1,3-butadiene is removed from the C4 cracking products by extraction or by selective hydrogenation to n-butenes. The C4 raffinate obtained, also referred to as raffinate I, contains predominantly the unsaturated butenes isobutene, 1-butene and 2-butene and also the hydrogenated products n-butane and isobutane. In the next step, isobutene is removed from the raffinate I and the isobutene-free C4 mixture obtained is referred to as raffinate II.

In industrial production, the removal of isobutene is carried out using various processes in which the relatively high reactivity of isobutene in the raffinate I is exploited. The reversible proton-catalyzed molecular addition of water to form tert-butanol or the molecular addition of methanol to form methyl tert-butyl ether are known. Isobutene can be recovered again from these addition products by redissociation (Weissermel, Arpe, Industrielle Organische Chemie, VCH Verlagsgesellschaft, 3rd edition, 1988, pages 74-79).

Likewise, the butadiene-free C4 raffinate can be brought into contact with an acidic suspended ion exchanger at elevated temperature and under superatmospheric pressure. Isobutene oligomerizes to diisobutene, triisobutene and to a small extent to higher oligomers. The oligomers are separated off from the unreacted C4 compounds. Diisobutene or triisobutene can then be obtained in pure form from the oligomerization mixture by distillation. Codimer is formed to a small extent by dimerization of n-butenes with isobutene (Weissermel, Arpe, Industrielle Organische Chemie, VCH Verlagsgesellschaft, 3rd edition, 1988, page 77; Hydrocarbon Processing, April 1973, pages 171-173).

Diisobutene, either prepared by oligomerization of pure isobutene obtained by redissociation or obtained during the course of the work-up of a butadiene-free raffinate I, is subsequently converted by means of the hydroformylation reaction or oxo reaction into a C9 derivative which has one more carbon atom. Since diisobutene contains predominantly the octenes 2,4,4-trimethyl-1-pentene and 2,4,4-trimethyl-2-pentene, the hydroformylation reaction gives the C9-aldehyde 3,5,5-trimethylhexanal as main constituent. Further C9 isomers which are present in small amounts are 3,4,4- and 3,4,5-trimethylhexanal and also 2,5,5-trimethylhexanal, 4,5,5-trimethylhexanal and 6,6-dimethylheptanal.

The isononanal prepared in this way can subsequently, as described above, be converted by reductive amination using ammonia and hydrogen into isononylamine or diisononylamine. Isononanal can also be reduced by means of hydrogen over a metal catalyst, for example over nickel or cobalt catalysts, to give isononanol and subsequently converted by means of the amination reaction into the corresponding isononylamines.

In view of the fact that the availability of octenes based on the C4 fraction from naphtha cracking is limited and depends on local site conditions, it is desirable to open up further octene sources on the basis of inexpensively available bulk products which can be transported in a simple way to the various sites. 2-Ethylhexanol is available at low cost as an industrial bulk product and can be marketed widely without problems. 2-Ethylhexanol is, as is known, prepared industrially by hydroformylation or oxo reaction of propylene to form n-butyraldehyde with subsequent alkali-catalyzed aldol condensation to form 2-ethylhexenal and subsequent total hydrogenation to 2-ethylhexanol (Ullmanns Encyklopadie der technischen Chemie, 4th edition, 1974, Verlag Chemie, volume 7, pages 214-215).

The use of 2-ethylhexanol for preparing an octene mixture which is processed by dehydration, hydroformylation and hydrogenation to give an isononanoic mixture is briefly described in WO 03/029180 A1. Here, setting of the viscosity of the isomeric dialkyl phthalates which are obtained by esterification of isomeric nonanols with phthalic acid or phthalic anhydride is the main focus. Information as to how to convert the dehydration products of 2-ethylhexanol into isononylamines is not given.

The utilization of 2-ethylhexanol as octene source makes it possible to provide isononylamines acid on the basis of propylene and reduces the dependence on the availability of octenes based on butene.

SUMMARY OF INVENTION

The present invention accordingly provides a process for preparing isononylamines starting out from 2-ethylhexanol. The process is characterized in that
(a) 2-ethylhexanol is dehydrated in the presence of a catalyst to form octene;
(b) the octene obtained in step a) is reacted with carbon monoxide and hydrogen in the presence of a transition metal compound of group VIII of the Periodic Table of the Elements to form isononanal; and
(c) the isononanal obtained in step b) is converted into isononylamines.

The present invention likewise provides isononylamines which can be obtained by
(a) dehydrating 2-ethylhexanol in the presence of a catalyst to form octene;
(b) reacting the octene obtained in step a) with carbon monoxide and hydrogen in the presence of a transition metal compound of group VIII of the Periodic Table of the Elements to form isononanal; and
(c) converting the isononanal obtained in step b) into isononylamines.

DETAILED DESCRIPTION

The dehydration of 2-ethylhexanol can be carried out either in the liquid phase or in the gas phase over a catalyst suitable for this purpose. The dehydration is preferably carried out in the gas phase at temperatures in the range from 200 to 450° C., preferably from 250 to 380° C., using conventional reactors in the presence of heterogeneous catalysts having dehydrating properties, e.g. aluminium oxide in its various modifications, nickel deposited on aluminium oxide or phosphoric acid deposited on silicon dioxide or aluminium oxide. Such heterogeneous catalysts suitable for dehydration are known from the prior art (GB 313426, U.S. Pat. No. 2,468,764, U.S. Pat. No. 2,919,973) and are commercially available as, for example, AI3996 from BASF SE. U.S. Pat. No. 2,919,973 is concerned with the dehydration of 2-ethylhexanol over a heterogeneous aluminium oxide catalyst at temperatures of about 350° C. and a space velocity over the catalyst of from 2.4 to 2.8 liters of 2-ethylhexanol per liter of catalyst an hour. However, the prior art gives no information on the isomer distribution in the octene mixture obtained.

The reactor used in the process of the invention for the dehydration of 2-ethylhexanol can contain not only the catalyst bed but also further packing elements or internals, for example Raschig rings, saddles, Pall rings, filter plates or column trays. If packing elements are used, they are preferably installed above the catalyst bed in order to reduce the dead volume. If dehydration is carried out in the liquid phase, internals and packing elements can be dispensed with, so that only the dehydration catalyst is present in the reaction vessel.

In the preferred mode of operation, 2-ethylhexanol is heated in an upstream vaporizer and passed in gaseous form over the catalyst bed, optionally using an inert carrier gas such as nitrogen, carbon dioxide or noble gases. The space velocity V/Vh over the heterogeneous catalyst can vary over a wide range and is generally from 0.2 to 3.5 liters of 2-ethylhexanol per liter of catalyst and hour. The reaction mixture taken off from the dehydration zone is subsequently condensed. Due to the eliminated water, an aqueous phase is formed and this is separated from the organic olefin phase by simple phase separation. The octene obtained is a mixture of structurally isomeric octenes having the singly branched octenes 2-ethyl-1-hexene and cis/trans 3-methyl-3-heptene and cis/trans 3-methyl-2-heptene as main components. Appreciable amounts of di-C8-ethers are not formed.

The octene present after removal of the water of dissociation is subsequently used without further purification or advantageously after purification by distillation for the reaction with carbon monoxide and hydrogen in the hydroformylation reaction or oxo reaction. The mixture of carbon monoxide and hydrogen used is also referred to as synthesis gas. The hydroformylation reaction is carried out in a homogeneous reaction system. The term homogeneous reaction system refers to a homogeneous solution composed essentially of solvent, if added, catalyst, olefinically unsaturated compound and reaction product. The relatively high-boiling condensation compounds of the aldehydes to be prepared, in particular the trimers of the aldehydes to be prepared, which are obtained as by-products in the hydroformylation and also their mixtures with the isononanal to be prepared have been found to be particularly effective solvents, so that a further addition of solvent is not absolutely necessary. However, in some cases an addition of solvent has been found to be advantageous. As solvents, use is made of organic compounds in which the starting material, reaction product and catalyst are soluble. Examples of such compounds are aromatic hydrocarbons such as benzene and toluene or the isomeric xylenes and mesitylene. Other solvents which can be used are paraffin oil, cyclohexane, n-hexane, n-heptane or n-octane, ethers such as tetrahydrofuran, ketones or Texanol® from Eastman. The proportion of solvent in the reaction medium can be varied over a wide range and is usually from 20 to 90% by weight, preferably from 50 to 80% by weight, based on the reaction mixture. However, the hydroformylation of the octene can also be carried out without addition of solvent.

The hydroformylation reaction is typically carried out in a homogeneous organic phase in the presence of at least one transition metal compound of group VIII of the Periodic Table of the Elements. The reaction can be carried out either in the presence or in the absence of complexing organoelement compounds which act as complexing ligands.

If the hydroformylation reaction is carried out in the presence of complexing ligands, the use of organophosphorous compounds as organoelement compounds is useful. Such complexes and their preparation are known (U.S. Pat. No. 3,527,809 A, U.S. Pat. No. 4,148,830 A, U.S. Pat. No. 4,247,486 A, U.S. Pat. No. 4,283,562 A). They can be used as uniform complexes or also as a mixture of various complexes. The transition metal concentration in the reaction medium extends over a wide range from about 1 to about 1000 ppm by weight and is preferably from 10 to 700 ppm by weight and in particular from 25 to 500 ppm by weight, in each case based on the homogeneous reaction mixture. As catalyst, it is possible to employ the stoichiometric transition metal complex. However, it has been found to be advantageous to carry out the hydroformylation in the presence of a catalyst system composed of transition metal complex and free complexing ligand which no longer undergoes complexation with the transition metal. The free complexing ligand can be the same one as that in the transition metal complex, but it is also possible to use complexing ligands different from this. Preferred complexing ligands include triarylphosphines such as triphenylphosphine, trialkylphosphines such as tri(cyclohexyl)phosphine, alkylphenylphosphines, organic phosphites or diphosphites. The molar ratio of transition metal to complexing ligand is generally from 1:1 to 1:1000 but can also be higher. Preference is given to using the transition metal and the complexing ligand in a molar ratio of from 1:3 to 1:500 and in particular from 1:50 to 1:300.

The hydroformylation reaction in the presence of complexing ligands is frequently also referred to as modified variant, which is usually carried out at temperatures of from 50 to 180° C., preferably from 100 to 160° C., and total pressures of from 0.2 to 30 MPa, preferably from 1 to 20 MPa.

The hydroformylation reaction can likewise be carried out in the absence of complexing ligands by the unmodified variant. Such transition metal catalysts which, for example, are not modified with phosphines or phosphites and their suitability as catalyst for hydroformylation are known from the literature and are referred to as unmodified transition metal catalysts. It is assumed in the technical literature that the transition metal compound $HM(CO)_4$ is the catalytically active transition metal species in the unmodified transition metal catalysis, although this has not been proven unambiguously because of the many chemical mechanisms proceeding side by side in the reaction zone. As transition metals of group VIII of the Periodic Table of the Elements, preference is given to using cobalt, rhodium, iridium, nickel, palladium, platinum, iron or ruthenium and in particular cobalt or rhodium. The modified or unmodified transition metal catalyst is formed under the conditions of the hydroformylation reaction from the transition metal compounds used, e.g. their salts such as chlorides, nitrates, sulphates, acetates, pentanoates, 2-ethylhexanoates or isononanoates, their chalcogenides, such as oxides or sulphides, their carbonyl compounds such as $M_2(CO)_8$, $M_4(CO)_{12}$, $M_6(CO)_{16}$, $M_2(CO)_9$, $M_3(CO)_{12}$, their organic transition metal compounds such as carbonyl-acetylacetonates or cyclooctadienyl-acetates or -chlorides, in the presence of carbon monoxide/hydrogen mixtures. Here, the transition metal compound can be used as solid or advantageously in solution. As transition metal compound which is used as catalyst precursor, it is possible to use, in particular, rhodium isononanoate, rhodium acetate, rhodium 2-ethylhexanoate or cobalt isononanoate, cobalt acetate or cobalt 2-ethylhexanoate, or $Co_2(CO)_8$, $Co_4(CO)_{12}$, $Rh_2(CO)_8$, $Rh_4(CO)_{12}$ or $Rh_6(CO)_{16}$ or cyclopentadienylrhodium compounds, rhodium acetylacetonate or dicarbonylrhodium acetylacetonate. Preference is given to using rhodium oxide and in particular rhodium acetate, rhodium 2-ethylhexanoate and rhodium isononanoate.

However, it is also possible firstly to preform the transition metal catalyst in a precarbonylation stage and subsequently introduce it into the actual hydroformylation stage. The conditions of preformation generally correspond to the hydroformylation conditions.

Since the use of transition metal catalysts which have not been modified with complexing ligands generally requires a lower transition metal content, the unmodified variant is generally carried out using an amount of transition metal from 1 to 100 ppm, preferably from 2 to 30 ppm, based on the octene used. Very particular preference is given to using rhodium or cobalt in an amount of from 2 to 30 ppm, preferably from 5 to 10 ppm, in each case based on the octene used.

The reaction of the octene with hydrogen and carbon monoxide to form isononanal according to the unmodified variant is advantageously carried out at relatively high pressures in the range from 5 to 70 MPa, preferably from 5 to 60 MPa and in particular from 10 to 30 MPa. Suitable reaction temperatures are in the range from 50 to 180° C., preferably from 50 to 150° C. and in particular from 100 to 150° C.

The composition of the synthesis gas, i.e. the proportions of carbon monoxide and hydrogen in the gas mixture, can vary within wide limits. In general, mixtures in which the molar ratio of carbon monoxide to hydrogen is from 5:1 to 1:5 are used. This ratio is usually 1:1 or deviates only slightly from this value. The olefinic compound can be introduced as such or in solution into the reaction zone. Suitable solvents are ketones such as acetone, methyl ethyl ketone, acetophenone, lower aliphatic nitriles such as acetonitrile, propionitrile or benzonitrile, dimethylformamide, linear or branched saturated aliphatic monohydroxy compounds such as methanol, ethanol, propanol and isopropanol, aromatic hydrocarbons such as benzene or toluene and saturated cycloaliphatic hydrocarbons such as cyclopentane or cyclohexane.

The hydroformylation stage can be carried out either batchwise or continuously. The desired aldehydes are isolated from the crude hydroformylation product by conventional methods, for example by distillation. Isononanal and further volatile components are taken off as overhead products and, if required, subjected to a further fine purification.

The amounts of transition metal used are obtained in the distillation residue and are, optionally after addition of fresh transition metal compound and removal of part of the aldehyde condensation products formed during the reaction, recirculated to the reaction zone.

The resulting mixture of isomeric isononanals is purified, advantageously by distillation, and subsequently converted by reductive amination into isononylamines. For the purposes of the present invention, the term reductive amination refers not only to the reaction of isononanal with ammonia, a primary or secondary amine and hydrogen in the presence of a conventional amination catalyst, in which primary, secondary and tertiary isononylamines are formed, but also to the corresponding reaction of isononanol, although no hydrogen is consumed in the amination or ammonolysis of the alcohol. If isononanol is used as starting material for the amine synthesis, isononanal is firstly hydrogenated in the presence of conventional hydrogenation catalysts by means of gas-phase or liquid-phase processes known per se to form isononanol. Suitable hydrogenation catalysts are, for example, nickel catalysts or copper catalysts, preferably nickel catalysts. The hydrogenations are generally carried out at hydrogen pressures of from 6 to 15 MPa and at temperatures of from 90 to 150° C. In a suitable process, hydrogenation is carried out in the gas phase over a copper catalyst in a first hydrogenation stage and subsequently in the liquid phase over a nickel catalyst in a second hydrogenation stage.

The reductive amination of both isononanal and of isononanol is carried out in reactors known to those skilled in the art, preferably over fixed-bed amination catalysts. Suitable reactors are, for example, tube reactors, including a bundle of a plurality of closely spaced parallel tubes. The tube reactors used can likewise contain packing elements or internals, for example Raschig rings, saddles, Pall rings, filter plates or column trays, and also optionally stirring devices. The suspension hydrogenation is less suitable. The process can be carried out either continuously or batchwise.

The starting material isononanal or isononanol can be reacted with a superstoichiometric or substoichiometric amount of ammonia and hydrogen depending on the desired degree of amination. In general, at least 0.2 mol, preferably from 0.3 to 40 mol, of ammonia is used per mol of starting material. The product distribution in respect of isononylamine, diisononylamine and triisononylamine can be controlled by the amount of ammonia used, with a higher excess of ammonia promoting the formation of the primary isononylamine. Apart from ammonia, it is also possible to use primary or secondary amines such as propylamine, n-butylamine, 2-ethylhexylamine, di-n-propylamine, di-n-butylamine or di-(2-ethylhexyl)amine, so as to give mixed diisononylamines and mixed triisononylamines. The reductive amination can be carried out solvent-free without addition of a solvent or diluent or with addition of solvents, for example methanol or ethanol (DE 199 35 448 A1).

The reaction components fed to the reductive amination can be in a gaseous or compressed state under the reaction conditions, with each reaction component or the mixture itself being able to be in various states of matter. In general, the reductive amination is carried out at temperatures in the range from 100 to 200° C., preferably from 110 to 150° C., and at pressures in the range from 0.1 to 40 MPa, preferably from 0.5 to 30 MPa.

Conventional amination catalysts containing at least one metal of transition groups 8 to 11 of the Periodic Table of the Elements, e.g. nickel, cobalt, platinum, palladium, iron, rhodium or copper, are used for the reductive amination of isononanal and isononanol. Preference is given to nickel or cobalt catalysts. Apart from unsupported catalysts such as Raney nickel or Raney cobalt, it is also possible to use supported catalysts. Suitable catalyst supports are all customary support materials, for example aluminium oxide, aluminium oxide hydrates in their various forms, silicon dioxide, polysilicic acids (silica gels) including kieselguhr, silica xerogels, magnesium oxide, zinc oxide, zirconium oxide and activated carbon. Apart from the main components, the catalytically active metal and support material, the amination catalysts can additionally contain additives in minor amounts, for example to improve the activity and/or operating life and/or selectivity of the catalysts. Such additives are known per se and include, for example, the oxides of calcium, barium, zinc, aluminium, zirconium and chromium. Nickel has been found to be the preferred catalytically active metal. Nickel catalysts on kieselguhr as support material with chromium as additive have been found to be particularly suitable for the reductive amination.

The reaction mixture taken off from the reactor is depressurized to atmospheric pressure via a high-pressure separator and subsequent depressurization devices and the crude isononylamines obtained are purified by known methods, for example by distillation, to produce in-specification product.

The isononylamines prepared starting out from 2-ethylhexanol by the process of the invention are, depending on the amination conditions, the primary isononylamine, diisononylamine or triisononylamine or mixed secondary or tertiary amines which contain at least one isononyl radical based on 2-ethylhexanol. The isononyl radical is a C9-hydrocarbon radical which is essentially unbranched or singly branched in the a position.

The isononylamines obtained are particularly suitable for use as corrosion inhibitors in lubricants.

The isononylamines obtained can likewise be used as auxiliary in rubber formulations and as vulcanization accelerators. They are likewise used as additives in lubricants, for example in the form of their dithiocarbamates or corresponding salts, e.g. molybdenum, zinc or sodium dithiocarbamates, for improving the abrasion resistance of mechanical apparatuses which are operated under high pressure.

The preparation of isononylamines starting out from 2-ethylhexanol is described in the following examples.

EXAMPLES

I. Dehydration of 2-Ethylhexanol

A fused silica tube which had a length of 1.3 meters and a diameter of 0.03 meter and in which the heated zone extended over 1.1 meters was used for the dehydration. The fused silica tube was charged with 250 ml of the acid catalyst AI 3996 from BASF SE in the form of 3×3 millimeter pellets. The dead volume was filled with glass rings.

2-Ethylhexanol was vaporized in an upstream vaporizer and conveyed with the aid of a stream of nitrogen as carrier gas at atmospheric pressure over the catalyst bed at a temperature of 350° C. and a space velocity of 0.5 liter per liter of catalyst volume and hour. The reaction mixture obtained was condensed in a downstream collection vessel and the aqueous phase was separated off. The organic phase obtained had the following composition determined by gas chromatography (% by area, in accordance with DIN 51405):

| | |
|---|---|
| First fraction/C4-C7-hydrocarbons | 0.3 |
| Other C8-olefins | 9.6 |
| 2-Ethyl-1-hexene | 7.6 |
| cis-3-Methyl-3-heptene | 14.6 |
| trans-3-Methyl-3-heptene | 28.8 |
| cis-3-Methyl-2-heptene | 16.2 |
| trans-3-Methyl-2-heptene | 23.9 |
| n-Octenes | 0.8 |
| Final fraction | 0.1 |

II. Hydroformylation of the Octene obtained in Step I.

The crude octene obtained from step I. was hydroformylated in the presence of 5 ppm of rhodium, added in the form of a solution of rhodium 2-ethylhexanoate in 2-ethylhexanol and based on octene used, at a temperature of 140° C. and a synthesis gas pressure of 19 MPa over a period of three hours. The molar composition of the synthesis gas was 1 mol of hydrogen to 1 mol of carbon monoxide. The crude hydroformylation product obtained had the following composition determined by gas chromatography (% by area, in accordance with DIN 51405):

| | |
|---|---|
| First fraction | 0.1 |
| C8-hydrocarbons | 8.5 |
| Intermediate fraction | 0.2 |
| Isononanal | 88.1 |
| n-Nonanal | 1.4 |
| Final fraction | 1.7 |

The results of further hydroformylation experiments using an octene obtained by dehydration of 2-ethylhexanol are shown in Table 1 below. Before use, the crude octene was distilled via a Claisen bridge to separate off the final fraction at a temperature at the top of 119-122° C. and atmospheric pressure. The starting octenes and the reaction products obtained were analysed by gas chromatography (reported in % by area, in accordance with DIN 51405).

TABLE 1

Hydroformylation of octenes obtained by dehydration of 2-ethylhexanol

| Example | IIa | IIb |
|---|---|---|
| Starting material | distilled | distilled |
| GC analysis of starting material (%) | | |
| First fraction/C4-C7-hydrocarbons | 0.3 | 0.4 |
| Other C8-Olefins | 5.9 | 7.7 |
| 2-Ethyl-1-hexene | 9.3 | 9.2 |
| cis-3-Methyl-3-heptene | 15.2 | 15.0 |
| trans-3-Methyl-3-heptene | 27.4 | 27.1 |
| cis-3-Methyl-2-heptene | 16.1 | 15.6 |
| trans-3-Methyl-2-heptene | 25.2 | 24.7 |
| n-Octenes | 0.5 | 0.2 |
| Final fraction | 0.1 | 0.1 |
| Experimental conditions | | |
| Rh concentration [ppm], based on octene used | 20 | 10 |
| Pressure [MPa] | 19 | 27 |
| Temperature [° C.] | 140 | 140 |
| Reaction time [h] | 2 | 2 |
| GC analysis of product (%) | | |
| First fraction | 0.1 | 0.1 |
| C8-hydrocarbons | 2.5 | 1.1 |
| Intermediate fraction | 0.3 | 0.1 |
| Isononanals | 90.8 | 94.7 |
| n-Nonanal | 2.0 | 1.4 |
| Final fraction | 4.3 | 2.6 |

The hydroformylation experiments carried out using triphenylphosphine as complexing ligand and the octene obtained by dehydration of 2-ethylhexanol are shown in Table 2 below. Undistilled material was used. The starting octenes and the reaction products obtained were analysed by gas chromatography (reported in % by area, in accordance with DIN 51405).

TABLE 2

Hydroformylation of octenes obtained by dehydration of 2-ethylhexanol, addition of triphenylphosphine

| Example | IIc | IId | IIe | IIf |
|---|---|---|---|---|
| Starting material | un-distilled, crude | un-distilled, crude | un-distilled, crude | un-distilled, crude |
| GC analysis of starting material (%) | | | | |
| C4-C7-hydrocarbons | 0.3 | 0.3 | 0.3 | 0.4 |
| Other C8-Olefins | 19.1 | 19.1 | 19.1 | 11.6 |
| 2-Ethyl-1-hexene | 7.9 | 7.9 | 7.9 | 8.6 |
| 3-Methyl-3-heptene | 36.5 | 36.5 | 36.5 | 40.0 |
| 3-Methyl-2-heptene | 36.2 | 36.2 | 36.2 | 39.3 |
| Final fraction | <0.01 | <0.01 | <0.01 | 0.1 |
| Experimental conditions | | | | |
| Rh concentration [ppm], based on octene used | 10 | 10 | 10 | 10 |
| Equivalents of TPP | 3 | 50 | 100 | 3 |
| Pressure [MPa] | 18 | 27 | 18 | 14 |
| Temperature [° C.] | 140 | 140 | 140 | 160 |
| Reaction time [h] | 1 | 2 | 1 | 2 |
| GC analysis of product (%) | | | | |
| First fraction | 0.1 | 0.1 | 0.1 | 0.1 |
| C8-hydrocarbons | 52.2 | 70.9 | 81.7 | 14.1 |
| Intermediate fraction | 0.8 | 0.1 | 0.1 | 1.9 |
| Isononanals | 45.7 | 28.3 | 17.6 | 76.1 |
| n-Nonanal | 0.5 | 0.1 | 0.1 | 0.5 |
| Final fraction | 0.7 | 0.4 | 0.4 | 7.3 |

Low boilers and unreacted olefin were firstly separated off as overhead product from the isononanal obtained in Example IIa in a 24 plate column at 200 hPa, a temperature at the bottom of 120° C. and a reflux ratio of 2:1. After low boilers had been separated off, the temperature at the bottom was increased to 140-150° C. and the isononanal was taken off at the top (boiling point in ° C. at 100 hPa: 110-114° C.), while high boilers remained in the distillation bottoms.

The isononanal obtained had the following composition determined by gas chromatography and was used for the subsequent hydrogenation.

TABLE 3

| Gas-chromatographic analysis (% by area, in accordance with DIN 51405) of the isononanal starting out from 2-ethylhexanol | |
|---|---|
| First fraction/C8-hydrocarbons | 0.2 |
| Intermediate fraction | 0.4 |
| 2-Ethyl-4-methylhexanal | 10.8 |
| 2-Propyl-3-methylpentanal | 3.6 |
| 2,5-Dimethylheptanal | 21.9 |
| 2,3-Dimethylheptanal (isomer) | 4.8 |
| 2,3-Dimethylheptanal (isomer) + 2-ethylheptanal | 8.4 |
| 2-Methyloctanal | 1.7 |
| 3-Ethylheptanal | 10.4 |
| 4-Methyloctanal | 20.6 |
| 4,5-Dimethylheptanal | 0.6 |
| 6-Methyloctanal | 11.0 |
| Other i-nonanals | 1.8 |
| n-Nonanal | 0.9 |
| Final fraction | 2.9 |

III. Hydrogenation of the Isononanal obtained in Step II. to Isononanol

The isononanal obtained and purified as per step IIa was placed together with the commercially available nickel catalyst Ni 55/5 from Johnson Matthey, which was used in an amount of 6% by weight based on the reaction mixture, in an autoclave and hydrogenated under a hydrogen pressure of 10 MPa and at a temperature of 100-130° C. for 2 hours.

The crude product obtained after the catalyst had been filtered off had the following composition determined by gas chromatography (% by area, in accordance with DIN 51405):

| First fraction | 1.3 |
|---|---|
| Intermediate fraction | 5.0 |
| Isononanol | 87.7 |
| n-Nonanal | 0.6 |
| Final fraction | 5.4 |

IV. Ammonolysis of the Isononanol obtained in Step III. to form Isononylamine

The isononanol obtained in step III. was placed together with the commercially available nickel catalyst Ni 52/35 from Johnson Matthey, which was used in an amount of 10% by weight, based on the reaction mixture, in an autoclave. A hydrogen pressure of 1.5 MPa was subsequently set and ammonia was introduced in a molar ratio of 8:1, based on isononanol.

The reaction mixture was heated to 250° C. and brought to a pressure of 29 MPa by introduction of hydrogen. After a reaction time of 8 hours, the reaction mixture was depressurized and the catalyst was filtered off.

The crude product obtained had the following composition determined by gas chromatography (% by area, in accordance with DIN 51405):

| First fraction | 7.6 |
|---|---|
| Isononanol | 13.3 |
| Isononylamine | 30.3 |
| Intermediate fraction | 8.5 |
| Diisononylamine* | 35.1 |
| Intermediate fraction | 1.6 |
| Triisononylamine | 3.5 |
| Final fraction/High boilers | 0.1 |

*including Schiff base containing the isononyl radical

V. Amination of the Isononanal obtained in Step II. to form Isononylamine

The isononanal obtained and purified as per step IIa was placed together with the commercially available nickel catalyst Ni 52/35 from Johnson Matthey, which was used in an amount of 5% by weight based on the reaction mixture, in an autoclave and aminatively hydrogenated under a hydrogen pressure of 10.2 MPa and at a temperature of 120° C. in the presence of 10 mol of ammonia per mol of isononanal for a period of 4 hours.

After depressurization of the reaction mixture, the nickel catalyst was filtered off and the reaction mixture was introduced into a phase separator in which the water of reaction formed separated from the organic phase. The crude organic product had the following composition determined by gas chromatography (% by area, in accordance with DIN 51405):

| First fraction | 1.2 |
|---|---|
| Isononanol | 28.3 |
| Isononylamine | 59.8 |
| Intermediate fraction | 0.6 |
| Diisononylamine* | 5.6 |
| Intermediate fraction | 0.4 |
| Triisononylamine | 2.5 |
| Final fraction/High boilers | 1.6 |

*including Schiff base containing the isononyl radical

VI. Preparation of Diisononylamine via the Corresponding Schiff Base by Reaction of the Isononylamine obtained in Step V. with the Isononanal obtained and Purified as per Step IIa To prepare the Schiff base, the isononylamine obtained in step V. was placed in a reaction vessel and the isononanal obtained and purified as per step IIa was added dropwise up to a molar ratio of 1 mol of isononylamine per 1.1 mol of isononanal. After a reaction time of three and a half hours at room temperature, the reaction mixture was introduced into a phase separator in which the water of reaction formed separated from the organic phase. The organic phase containing the Schiff base was placed together with the commercially available nickel catalyst Ni 52/35 from Johnson Matthey, which was used in an amount of 5% by weight based on the reaction mixture, in an autoclave and hydrogenated under a hydrogen pressure of 10 MPa and at a temperature of 120° C. for a period of 6 hours. The crude product obtained after the catalyst had been filtered off had the following composition determined by gas chromatography (% by area, in accordance with DIN 51405):

| First fraction | 9.7 |
|---|---|
| Isononanol | 3.9 |
| Isononylamine | 4.5 |
| Intermediate fraction | 4.8 |
| Diisononylamine* | 62.6 |
| Intermediate fraction | 0.4 |
| Triisononylamine | 14.0 |
| Final fraction/High boilers | 0.1 |

*including Schiff base containing the isononyl radical

VII. Preparation of Triisononylamine by Ammonolysis of the Isononanol obtained in Step III.

The isononanol obtained in step III. was placed together with the conventionally available nickel catalyst Ni 55/5 from Johnson Matthey, which was used in an amount of 5% by weight based on the reaction mixture, in a stirred vessel. Hydrogen was subsequently passed at atmospheric pressure in an amount of five standard liters per hour through the reaction solution and, in parallel thereto, ammonia was introduced in an amount of 0.9 mol of ammonia per mol of isononanol over a period of 3 hours. The water of reaction formed was removed azeotropically. After 3 hours, the reaction was stopped and the catalyst was filtered off. The crude product obtained had the following composition determined by gas chromatography (% by area, in accordance with DIN 51405):

| First fraction | 1.5 |
|---|---|
| Isononanol | 6.8 |
| Isononylamine | 1.4 |
| Diisononylamine* | 1.1 |
| Intermediate fraction | 0.1 |
| Triisononylamine | 89.0 |
| Final fraction/High boilers | 0.1 |

*including Schiff base containing the isononyl radical

The invention claimed is:

1. Process for preparing isononylamines starting out from 2-ethylhexanol, characterized in that
   (a) 2-ethylhexanol is dehydrated in the presence of a catalyst to form a mixture of structurally isomeric octenes with the singly branched octenes 2-ethyl-1-hexene and cis/trans-3-methyl-3-heptene and cis/trans-3-methyl-2-heptene as components;
   (b) the octene obtained in step a) is reacted with carbon monoxide and hydrogen in the presence of a transition metal compound of group VIII of the Periodic Table of the Elements to form isononanal; and
   (c) the isononanal obtained in step b) is converted into isononylamines, the isononyl radicals of which comprise unbranched radicals or singly branched radicals in the $\alpha$ position.

2. Process according to claim 1, characterized in that aluminium oxide, nickel deposited on aluminium oxide, or phosphoric acid deposited on silicon dioxide or aluminium oxide is used as catalyst in step a).

3. Process according to claim 1, characterized in that 2-ethylhexanol is dehydrated in the gas phase in step a).

4. Process according to claim 1, characterized in that a cobalt or rhodium compound is used as transition metal compound of group VIII of the Periodic Table of the Elements in step b).

5. Process according to claim 1, characterized in that the reaction in step b) is carried out in the absence of complexing organoelement compounds.

6. Process according to claim 1, characterized in that the isononanal obtained in step b) is distilled.

7. Process according claim 1, characterized in that the isononanal obtained in step b) is, in step c), reacted with ammonia, a primary or secondary amine and hydrogen in the presence of an amination catalyst to form isononylamines.

8. Process according to claim 1, characterized in that the isononanal obtained in step b) is, in step c), hydrogenated by means of hydrogen in the presence of a hydrogenation catalyst to form isononanol and subsequently reacted with ammonia, a primary or secondary amine and hydrogen in the presence of an amination catalyst to form isononylamines.

9. Process according to claim 1, characterized in that a nickel or cobalt catalyst is used as amination catalyst.

10. Isononylamines which can be obtained by
    (a) dehydrating 2-ethylhexanol in the presence of a catalyst to form a mixture of structurally isomeric octenes with the singly branched octenes 2-ethyl-1-hexene and cis/trans-3-methyl-3-heptene and cis/trans-3-methyl-2-heptene as components;
    (b) reacting the octene obtained in step a) with carbon monoxide and hydrogen in the presence of a transition metal compound of group VIII of the Periodic Table of the Elements to form isononanal; and
    (c) converting the isononanal obtained in step b) into isononylamines, the isononyl radicals of which comprise unbranched radicals or singly branched radicals in the $\alpha$ position.

11. The isononylamines according to claim 10 incorporated into lubricant compositions as corrosion inhibitors.

12. A method of making rubber compositions comprising preparing isononylamines starting out from 2-ethylhexanol, characterized in that (a) 2-ethylhexanol is dehydrated in the presence of a catalyst to form octene; (b) the octene obtained in step a) is reacted with carbon monoxide and hydrogen in the presence of a transition metal compound of group VIII of the Periodic Table of the Elements to form isononanal; and (c) the isononanal obtained in step b) is converted into the isononylamines and incorporating the isononylamines so prepared into the rubber compositions as auxiliaries.

13. A method of making rubber compositions comprising preparing isononylamines starting out from 2-ethylhexanol, characterized in that (a) 2-ethylhexanol is dehydrated in the presence of a catalyst to form; (b) the octene obtained in step a) is reacted with carbon monoxide and hydrogen in the presence of a transition metal compound of group VIII of the Periodic Table of the Elements to form isononanal; and (c) the isononanal obtained in step b) is converted into the isononylamines and incorporating the isononylamines so prepared into the rubber compositions as vulcanization accelerators.

14. A method for improving the abrasion resistance of mechanical apparatuses operated under pressure comprising incorporating the isononylamines according to claim 1 into a lubricant composition applied to said apparatus.

15. A method for improving the abrasion resistance of mechanical apparatuses operated under pressure comprising preparing isononylamines starting out from 2-ethylhexanol, characterized in that (a) 2-ethylhexanol is dehydrated in the presence of a catalyst to form octene; (b) the octene obtained in step a) is reacted with carbon monoxide and hydrogen in the presence of a transition metal compound of group VIII of the Periodic Table of the Elements to form isononanal; and (c) the isononanal obtained in step b) is converted into the isononylamines and incorporating isononylamines into a lubricant composition applied to said apparatus, further characterized in that the isononylamines so prepared are used in the form of their isononyldithiocarbamates or corresponding salts.

16. The method according to claim 15, characterized in that the isononylamines so prepared are used in the form of their molybdenum, zinc or sodium isononyldithiocarbamates.

17. Process according to claim 2, characterized in that 2-ethylhexanol is dehydrated in the gas phase in step a).

18. Process according to claim 2, characterized in that a cobalt or rhodium compound is used as transition metal compound of group VIII of the Periodic Table of the Elements in step b).

19. Process according to claim 3, characterized in that a cobalt or rhodium compound is used as transition metal compound of group VIII of the Periodic Table of the Elements in step b).

20. Process according to claim 1, characterized in that the octene obtained in step a) consists predominantly of methyl heptenes.

21. Process according to claim 1, wherein 2-ethylhexanol is dehydrated in the presence of a catalyst to form a mixture of structurally isomeric octenes with the singly branched octenes 2-ethyl-1-hexene and cis/trans-3-methyl-3-heptene and cis/trans-3-methyl-2-heptene as components comprising more than 50% of the mixture up to about 93.7% of the mixture as measured by gas chromatography, % area.

* * * * *